(12) United States Patent
Kramer et al.

(10) Patent No.: US 6,290,934 B1
(45) Date of Patent: Sep. 18, 2001

(54) AGENT FOR THE PROMOTION OF ORAL HYGIENE AND ORAL HEALTH

(75) Inventors: Axel Kramer, Georg-Engel-Strasse 20, D-17489, Greifswald; Michael Rosin, Greifswald, both of (DE)

(73) Assignee: Axel Kramer, Greifswald (DE)

( * ) Notice: Subject to any disclaimer, the term of this patent is extended or adjusted under 35 U.S.C. 154(b) by 0 days.

(21) Appl. No.: 09/392,611

(22) Filed: Sep. 9, 1999

Related U.S. Application Data

(63) Continuation-in-part of application No. PCT/EP98/01340, filed on Mar. 7, 1998.

(30) Foreign Application Priority Data

Mar. 12, 1997 (DE) ............................................. 197 10 068

(51) Int. Cl.⁷ .............................. A61K 7/16; A61K 7/20; A61K 31/26
(52) U.S. Cl. ................................................. 424/53; 424/49
(58) Field of Search ......................................... 424/49–58

(56) References Cited

U.S. PATENT DOCUMENTS

| | | | |
|---|---|---|---|
| 4,537,764 | * 8/1985 | Pellic et al. ............................. | 424/50 |
| 4,861,582 | 8/1989 | Pollock et al. . | |
| 4,978,528 | * 12/1990 | Detre ..................................... | 424/616 |
| 4,980,152 | 12/1990 | Fraizier et al. . | |
| 5,453,284 | * 9/1995 | Pellico ................................... | 424/50 |
| 5,503,853 | * 4/1996 | Bollon et al. ......................... | 424/607 |
| 5,607,681 | * 3/1997 | Galley et al. ......................... | 424/405 |
| 5,820,841 | * 10/1998 | Chintal ................................. | 423/305 |

FOREIGN PATENT DOCUMENTS 0332551  2/1989 (EP) .

OTHER PUBLICATIONS

Pruitt, K.M., et al., "Limiting Factors for the Generation of Hypothiocyanite Ion, an Antimicrobial Agent, in Human Saliva," *Caries Res.*, vol. 16, pp 315–323, (1982).

Tenovuo, J., et al., "Relationship of the Human Salivary Peroxidase System to Oral Health," *Journal of Oral Pathology*, vol. 13, pp 573–584, (1984).

Muhlemann, H.R., et al., "Gingival Sulcus Bleeding—a Leading Symptom in Initial Gingivitis," *Helv. Odont. Aeta*, vol. 15, pp 107–113, (1971).

Silness, John, et al., "Periodontal Disease in Pregnancy; II. Correlation Between Oral Hygiene and Periodontal Condition," *Aeta Odont. Scand.*, vol. 22, pp 121–135, (1964).

Wohlrab, W., "Bedentung von Harnstoff in der Externen Therapie," *Der Hautharzt*, vol. 40, Supplement 9 (1989).

* cited by examiner

Primary Examiner—Shep K. Rose
(74) Attorney, Agent, or Firm—Brobeck, Phleger & Harrison

(57) ABSTRACT

The present invention relates to agents for the promotion of oral hygiene and oral health, especially for the inhibition of bacterial plaque accumulation on teeth, dental prostheses and respective adjacent surfaces, for the prophylaxis and therapy of inflammations and diseases of the oral mucosa, gingiva, periodontium, and for caries prophylaxis.

Agents for the promotion of oral hygiene and oral health, comprising ionically bound or free thiocyanate ions and carbamide perhydrate in addition to per se known additives and vehicles.

10 Claims, No Drawings

AGENT FOR THE PROMOTION OF ORAL HYGIENE AND ORAL HEALTH

This application is a continuation-in-part of International Application No. PCT/EP98/01340 designating the United States filed on Mar. 7, 1998, the text of which is incorporated herein by reference.

The present invention relates to compositions for the promotion of oral hygiene and oral health, especially for the inhibition of bacterial plaque accumulation on teeth, dental prostheses and respective adjacent surfaces, for the prophylaxis and therapy of inflammations and diseases of the oral mucosa, gingiva, periodontium, and for caries prophylaxis.

For the prophylaxis and therapy of oral diseases, especially inflammatory diseases of the periodontium and caries, a variety of antibiotic, antiseptic and antiphlogistic agents are employed. The use of antibiotics (also local use, since a major part of the agents is administered orally by swallowing) is a radical intervention in the physiological bacterial flora of the digestive tract including the oral cavity. The same applies to antiseptics which, in this indication, are exclusively used in local application, i.e. in the oral cavity. Antiphlogistic agents, for their part, can only influence affected tissues, but fail to offer a possibility for the prophylaxis of oral diseases. In addition, the use of non-physiological substances, such as antibiotic, antiseptic and antiphlogistic agents, involves all the risks of known medicamental side-effects, including the development of microbial resistance against antibiotics. It is known that the support of physiological bacterial defense systems, such as the lactoperoxidase system of saliva, can have a positive effect on oral health (Tenovuo et al.: Relationship of the human salivary peroxidase system to oral health; J. Oral Path. 13: 573–584, 1984). Since, according to studies made by Pruitt K. M. et al. (Limiting factors of the generation of hypothiocyanite ion, an antimicrobial agent, in human saliva; Caries Res. 16: 315–323, 1982), the bioavailability of hydrogen peroxide in saliva limits the in-vivo effectivity of the lactoperoxidase system, agents have been introduced which contain enzymes for forming hydrogen peroxide in saliva. These systems have the following disadvantages:

no direct provision of hydrogen peroxide;

when factors inhibiting the enzymes which form the hydrogen peroxide exist in the oral cavity, the formation of hydrogen peroxide cannot take place to the desired extent;

hindering of physiological penetration processes in the tissue by the formation of hydrogen peroxide at the tissue interfaces.

It has been the object of the invention to prevent, heal or alleviate diseases in the oral cavity, especially inflammatory diseases due to bacteria. In particular, damage to the physiological bacterial flora of the gastro-intestinal tract and the oral cavity and danger from medicamental side-effects are to be avoided by dispensing with the use of non-physiological xenobiotic active substances, for example, antibiotics, plaque-inhibiting agents, antiphlogistics.

Thus, it has been the object of the invention to develop novel effective agents for the prophylaxis, therapy and alleviation of diseases of the oral mucosa and the dental supporting system, which agents involve physiological compounds and bring about a purposeful promotion of physiological antibacterial defense mechanisms, physiological healing and repair processes and physiological detoxification mechanisms in the oral cavity and are undangerous in use.

In a first embodiment of the invention, the above object is achieved by agents for the promotion of oral hygiene and oral health, comprising ionically bound or free thiocyanate ions and carbamide perhydrate (also known as carbamide hydrogen peroxide) in addition to per se known additives and vehicles.

Thiocyanate is a physiological substance which naturally occurs in the saliva and which is innocuous to humans and animals in the quantities to be employed. Carbamide perhydrate is a urea/hydrogen peroxide adduct in a 1:1 ratio and is thus a combination of two physiological active substances.

It is particularly preferred according to the present invention that the thiocyanate ions are present in the form of alkali metal salts including ammonium salts and their derivatives. Thus, the thiocyanates are ionizable in contrast to organic, covalently bound thiocyanates.

It is particularly preferred according to the present invention that the alkali metal salts of the thiocyanates are selected from sodium, potassium and ammonium thiocyanate.

According to the present invention, it is particularly preferred that the agents contain from 0.3 to 30 g/kg of thiocyanate ions.

The use of the directly hydrogen peroxide forming carbamide perhydrate instead of enzymatically formed hydrogen peroxide as the following advantages:

provision of hydrogen peroxide by direct cleavage rather than by a detour via biochemical formation, which is also susceptible to interferences;

improvement of active substance penetration by urea released from carbamide perhydrate (Wohlrab W.: Bedeutung von Harnstoff in der externen Therapie, Hautarzt 40, Suppl. 9: 1981).

It is particularly preferred according to the present invention that the weight ratio of thiocyanate ions to carbamide perhydrate is adjusted within a range of from 10:1 to 1:10, especially 5:1 to 1:5.

The combination according to the invention of thiocyanate at concentrations in the range according to the invention with carbamide perhydrate leads to surprising novel effects which could not be seen when the individual active substances are used alone or when the concentration of thiocyanate in the combination is lower. This novel quality of activity could be confirmed in a clinically significant manner, substantiated through the parameters sulcus bleeding index (Mühlemann H. R. and Son S.: Gingival sulcus bleeding—a leading symptom in initial gingivitis. Helv. odont. Acta 15: 107–11, 1973), plaque index (Silness, J. and Löe, H.: Periodontal disease in pregnance: Correlation between oral hygiene and periodontal condition. Acta odont. Scand. 22: 121–135, 1964), and measurement of gingival fluid quantities (Periotron 6000).

In addition to the active ingredients, thiocyanate and carbamide perhydrate, the agents according to the invention contain as additives and vehicles, in particular, cleaning particulates, humectants, binders, thickeners, preservatives, fluoride compounds, foaming agents, surfactants, sweeteners, colorants and/or flavoring agents. By way of example, there may be mentioned hydroxyethylcellulose, methylparabene, saccharin, menthol, peppermint oil and/or distilled water.

The agents according to the invention can be used, in particular, in various formulations, for example, pastes, gels, mouth washes, suspensions, sprays, granules, powders and chewing gums; preferably, the thiocyanate ions and the carbamide perhydrate are provided separately, for example, in separated compartments to effect mixing only immediately prior to or during the application.

The application of the agents according to the invention can be effected with any of a variety of techniques, the use as a tooth paste or tooth gel for daily dental and oral hygiene at home and the use as a mouth wash in connection with or for the daily oral hygiene being particularly effective. For specific indications, special applications by dentists or dental staff are intended, for example, for the treatment of periodontal pockets on the dental supporting system.

EXAMPLE 1

Thiocyanate ($SCN^-$) and carbamide perhydrate (CPH) were examined in dental hygiene gels together with conventional additives and vehicles in various combinations and concentrations in a randomized, double-blind and placebo controlled clinical study for the inhibition of plaque accumulation and the influence on the health condition of the gingiva. 140 test persons in 6 study groups used the tooth hygiene gels over a period of 8 weeks.

TABLE 1

| Group | $SCN^-$ | CPH |
| --- | --- | --- |
| group A (placebo)* n = 40 | 0 | 0 |
| group B* n = 20 | 0.1% by weight | 0 |
| group C* n = 20 | 0.5% by weight | 0 |
| group D n = 20 | 0.1% by weight | 0.1% by weight |
| group E n = 20 | 0.5% by weight | 0.1% by weight |
| group F* n = 20 | 0 | 0.1% by weight |

*comparison

Both thiocyanate alone (groups B and C) and carbamide perhydrate alone (group F) had no influence on plaque and gingivitis (Tables 3 and 4). Also, the combination of 0.1% by weight of carbamide perhydrate with the relatively small thiocyanate concentration of 0.1% by weight (group D) had no influence on the parameters examined (Tables 2 to 4). In contrast, the combination of 0.1% by weight of carbamide perhydrate with the fivefold thiocyanate concentration (0.5% by weight) (group E) led to a statistically significant reduction of plaque and the two gingivitis parameters (Tables 2 to 4).

TABLE 2

Sulcus fluid flow rate (Periotron 6000) in groups with different $SCN^-$/CPH dental hygiene gels

| group/day of examination | first examination | 1 week | 4 weeks | 8 weeks |
| --- | --- | --- | --- | --- |
| group A n = 36 | 23.4 ± 13.9 | 22.2 ± 14.7 | 20.8 ± 14.6 | 18.6 ± 12.9 |
| group B n = 17 | 23 ± 9.8 | 22.5 ± 12.6 | 20.5 ± 10.5 | 20.4 ± 13.2 |
| group C n = 16 | 27.5 ± 19.6 | 25 ± 16.5 | 16.4 ± 10.7[2] | 25.9 ± 15.6 |
| group D n = 15 | 23.7 ± 15.9 | 19.7 ± 12 | 14.1 ± 12.3 | 24.2 ± 13.8 |
| group E n = 16 | 22.5 ± 14.8 | 17.5 ± 11.9 | 15.5 ± 10.4 | 11.8 ± 8.1[3] |
| group F n = 18 | 23 ± 14.5 | 23.5 ± 10.9 | 16.1 ± 7.8[1] | 12.1 ± 8.2[3] |

[1] $P=0.90$
[2] $P=0.95$
[3] $P=0.99$

Significance of the deviation of the average from the average of the first examination:

TABLE 3

Plaque index in groups with different $SCN^-$/CPH dental hygiene gels

| group/day of examination | first examination | 1 week | 4 weeks | 8 weeks |
| --- | --- | --- | --- | --- |
| group A n = 36 | 0.336 ± 0.26 | 0.345 ± 0.27 | 0.339 ± 0.19 | 0.36 ± 0.24 |
| group B n =0 17 | 0.383 ± 0.23 | 0.416 ± 0.29 | 0.45 ± 0.48 | 0.505 ± 0.35 |
| group C n = 16 | 0.444 ± 0.37 | 0.388 ± 0.28 | 0.447 ± 0.41 | 0.419 ± 0.28 |
| group D n = 15 | 0.355 ± 0.34 | 0.283 ± 0.22 | 0.307 ± 0.21 | 0.355 ± 0.22 |
| group E n = 16 | 0.452 ± 0.29 | 0.338 ± 0.26 | 0.309 ± 0.25 | 0.277 ± 0.29[1] |
| group F n = 18 | 0.438 ± 0.24 | 0.372 ± 0.30 | 0.345 ± 0.2 | 0.295 ± 0.32 |

[1] $P=0.90$
[2] $P=0.95$
[3] $P=0.99$

Significance of the deviation of the average from the average of the first examination:

TABLE 4

Sulcus bleeding index in groups with different $SCN^-$/CPH dental hygiene gels

| group/day of examination | first examination | 1 week | 4 weeks | 8 weeks |
| --- | --- | --- | --- | --- |
| group A n = 36 | 1.083 ± 0.37 | 1.007 ± 0.33 | 1.073 ± 0.41 | 1.040 ± 0.52 |
| group B n = 17 | 1.298 ± 0.58 | 1.175 ± 0.59 | 1.227 ± 0.72 | 1.219 ± 0.68 |
| group C n = 16 | 1.112 ± 0.46 | 1.051 ± 0.55 | 1.057 ± 0.57 | 1.14 ± 0.58 |
| group D n = 15 | 1.005 ± 0.34 | 0.872 ± 0.35 | 0.995 ± 0.27 | 0.993 ± 0.37 |
| group E n = 16 | 1.129 ± 0.38 | 0.963 ± 0.43 | 0.904 ± 0.41 | 0.818 ± 0.36[2] |
| group F n = 18 | 1.266 ± 0.48 | 1.234 ± 0.42 | 1.117 ± 0.29 | 1.114 ± 0.53 |

[1] $P=0.90$
[2] $P=0.95$
[3] $P=0.99$

Significance of the deviation of the average from the average of the first examination:

What is claimed is:

1. An agent for the promotion of oral hygiene and oral health, comprising ionically bound or free thiocyanate ions and a 1:1 urea/hydrogen peroxide adduct (carbamide perhydrate), comprising from 0.3 to 30 g of carbamide perhydrate per kg and from 0.3 to 30 g thiocyanate ions per kg.

2. The agent according to claim 1, wherein said thiocyanate ions are present in the form of alkali metal salts.

3. The agent according to claim 2, wherein said alkali metal salts are selected from sodium, potassium and ammonium thiocyanate.

4. The agent according to claim 1, wherein the weight ratio of thiocyanate ions to carbamide perhydrate is within a range of from 10:1 to 1:10.

5. The agent according to claim 1, further comprising additives and vehicles selected from the group consisting of cleaning particulates, humectants, binders, thickeners, preservatives, fluoride compounds, foaming agents, surfactants, sweeteners, colorants, flavoring agents, and combinations thereof.

6. The agent according to claim 1, wherein the agent is in the form of a paste, gel, mouth wash, suspension, spray, granule, powder or chewing gum.

7. The agent according to any one of claim 1, 2, 3, 4, 5, or 6 for inhibiting bacterial plaque accumulation on teeth, dental prostheses and adjacent surfaces, for the prophylaxis, therapy and alleviation of inflammations and diseases of the oral mucosa, gingiva, and periodontium, for caries prophylaxis, or combinations thereof.

8. The agent according to any one of claim 1, 2, 3, 4, 5, or 6 wherein said thiocyanate ions and carbamide perhydrate are present in the spatially separated configuration.

9. The agent according to claim 4, wherein the weight ratio of thiocyanate ions to carbamide perhydrate is within a range of from 5:1 to 1:5.

10. A method for inhibiting bacterial plaque accumulation on teeth, dental prostheses and adjacent surfaces, for the prophylaxis, therapy and alleviation of inflammations and diseases of the oral mucosa, gingiva, and periodontium, for caries prophylaxis, or combinations thereof, said method comprising oral application of an agent according to claim 7.

* * * * *